(12) United States Patent
Kupiecki

(10) Patent No.: US 6,638,243 B2
(45) Date of Patent: *Oct. 28, 2003

(54) BALLOON CATHETER WITH DELIVERY SIDE HOLES

(75) Inventor: David Kupiecki, Cupertino, CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/211,399

(22) Filed: Aug. 2, 2002

(65) Prior Publication Data

US 2003/0004461 A1 Jan. 2, 2003

Related U.S. Application Data

(63) Continuation of application No. 08/539,943, filed on Oct. 6, 1995, now Pat. No. 6,440,097.

(51) Int. Cl.[7] .............................................. A61M 25/00
(52) U.S. Cl. ............................... 604/49; 604/53; 604/96
(58) Field of Search ................. 604/52, 53, 49, 604/96, 102, 33, 99, 101, 103, 167, 170, 246, 249, 271, 280; 606/191–197; 600/433–435, 585

(56) References Cited

U.S. PATENT DOCUMENTS

| | | |
|---|---|---|
| 3,923,065 A | 12/1975 | Nozick et al. |
| 4,471,779 A | 9/1984 | Antoshkiw et al. |
| 4,606,347 A | 8/1986 | Fogarty et al. |
| 4,641,654 A | 2/1987 | Samson et al. |
| 4,739,768 A | 4/1988 | Engelson |
| 4,813,934 A | 3/1989 | Engelson et al. |
| 4,983,166 A | 1/1991 | Yamawaki |
| 5,085,636 A | 2/1992 | Burns |
| 4,813,934 A | 5/1992 | Engelson et al. |
| 5,116,317 A | 5/1992 | Carson, Jr. et al. |
| 5,171,221 A | 12/1992 | Samson |
| 5,304,198 A | 4/1994 | Samson |

(List continued on next page.)

FOREIGN PATENT DOCUMENTS

| | | |
|---|---|---|
| DE | 39 38 727 A1 | 10/1990 |
| EP | 0 098 100 A3 | 1/1984 |
| WO | WO 95/11719 A1 | 5/1995 |

OTHER PUBLICATIONS

Mandai et al., "Direct Thrombosis of Aneurysms with Cellulose Acetate Polymer. Part I. Results of Thrombosis in Experimental Aneurysms," *J. Neurosurg. (1992) 77:497–500.*

(List continued on next page.)

*Primary Examiner*—Jeffrey R. Jastrzab
(74) *Attorney, Agent, or Firm*—Crompton, Seager & Tufte, LLC

(57) ABSTRACT

This is a medical catheter made up of a body having on its distal end portion an expandable balloon and, proximal of the balloon, a delivery lumen ending in a port through which therapeutic or diagnostic agents may be delivered. In one variation, a single inflation/wire lumen extends from the catheter proximal end to the catheter distal end, through which the balloon is inflated with pressurized fluid and through which a guide wire extends. The guide wire may have a valve plug for selectively seating against a valve seat of the catheter distal end to seal the inflation/wire lumen for balloon inflations. In another variation, a vaso-occlusive agent is disposable within a delivery lumen in a catheter coupled with a steerable guidewire. The delivery lumen ends in a delivery port near to and proximal of an expandable balloon located at the catheter's end. A single inflation/wire lumen may also be provided for facilitating both balloon inflation and guide wire tracking.

22 Claims, 2 Drawing Sheets

U.S. PATENT DOCUMENTS

| | | |
|---|---|---|
| 5,314,443 A | 5/1994 | Rudnick |
| 5,320,604 A | 6/1994 | Walker et al. |
| 5,324,259 A | 6/1994 | Taylor et al. |
| 5,324,269 A | 6/1994 | Miraki |
| 5,356,388 A | 10/1994 | Sepetka et al. |
| 5,368,567 A | 11/1994 | Lee |
| 5,370,615 A | 12/1994 | Johnson |
| 5,413,581 A | 5/1995 | Goy |
| 5,415,636 A | 5/1995 | Forman |
| 5,431,639 A | 7/1995 | Shaw |
| 5,437,632 A | 8/1995 | Engelson et al. |
| 5,439,446 A | 8/1995 | Barry |
| 4,739,768 A | 10/1995 | Engelson |
| 5,458,615 A | 10/1995 | Klemm et al. |
| 5,486,195 A | 1/1996 | Myers et al. |
| 5,533,987 A | 7/1996 | Pray et al. |
| 5,538,513 A | 7/1996 | Okajima |
| 5,637,086 A | 6/1997 | Ferguson et al. |
| 5,688,237 A | 11/1997 | Rozga et al. |
| 5,700,243 A | 12/1997 | Narciso, Jr. |
| 6,440,097 B1 | 8/2002 | Kupiecki |

OTHER PUBLICATIONS

Sugawara et al., "Experimental Investigations Concerning a New Liquid Embolization Method: Combined Administration of Ethanol–Estrogen and Polyvinyl Acetate," *Neurol. Med. Chir.*(Tokyo),(1993) 33:71–76.

Taki et al., "A New Liquid Material for Embolization of Arterivenous Malformations," *AJNR (1990) 11:163–168.*

BALLOON CATHETER WITH DELIVERY SIDE HOLES

This application is a continuation of application Ser. No. 08/539,943, filed Oct. 6, 1995 Now U.S. Pat. No. 6,440,097.

FIELD OF THE INVENTION

This invention is a medical device. More specifically, it is a balloon catheter having a lumen with a port proximal of a balloon through which therapeutic or diagnostic agents may be delivered.

BACKGROUND OF THE INVENTION

Balloon Catheter Overview

Balloon catheters are medical devices that have been used to facilitate percutaneous medical treatment such as pressure monitoring, cardiac output and flow monitoring, angioplasty, artificial vaso-occlusion, and cardiac support. Balloon catheters generally have an elongated shaft with a fluid expandable balloon on the distal end and a coupler on the proximal end. Balloon catheter designs generally include a lumen that extends from the coupler end to the balloon end and facilitates delivery of fluid therethrough for inflating the balloon. One way that balloon catheters may be classified is by the way they are adapted for delivery into remote in-vivo sites. Among such balloon catheter categories are "flow-directed," "over-the-wire," "fixed-wire," and "single-lumen" balloon catheters.

"Flow-directed" balloon catheters are generally balloon catheters in which the balloon is inflated at a low pressure and acts like a sail in the blood stream. The inflated balloon, along with the attached catheter, is pulled downstream to a remote location by the blood flow acting on the inflated balloon.

"Over-the-wire" balloon catheters are generally balloon catheters that slideably track over an independent wire rail to a distally remote location. Generally, a radiopaque, steerable guide wire may be negotiated, via radiographic visualization, to a desired remote location such as a distal site in the vascular tree. Over-the-wire catheters generally have two lumens. A first lumen, the guide wire lumen, is used for slidably receiving and tracking over a steerable guide wire. The guide wire lumen often extends substantially the full length of the catheter and terminates at each end in open ports. Alternatively, the guide wire lumen may extend only between a distal port and a proximal port that is situated on the catheter distally of the catheter's proximal end. The second lumen terminates at a distal end in a sealed, expandable balloon, and at the opposite proximal end in an open port. The proximal open end may be coupled with a pressurizable fluid source for inflating and deflating the balloon.

When a guide wire lumen extends the length of the catheter and the proximal port is accessible to a doctor during in-vivo use, there is a benefit in being able to exchange multiple wires slideably through the guide wire lumen. The balloon catheter is kept in place as a conduit delivery device for such guide wire exchanges—the wires do not need to be re-steered and tracked to the desired site each time. Also, this full length co-axial arrangement between catheter and wire allows manipulation of the wire's placement during balloon inflation. This may be desirable, for instance, for seating the wire in a side vessel distal to the balloon inflation site to retain access thereto in the case the vasculature distal to the inflation site collapses during the artificial total occlusion created by the balloon.

In contrast to the features just described, over-the-wire catheters may alternatively have the guide wire lumen extend only along a distal portion of the catheter length, with the proximal guide wire port disposed distally to the catheter proximal end. With this type of over-the-wire design, a shortened length of catheter rides co-axially on the wire. As such, a much shorter wire may be used (compared to full length co-axial over-the-wire designs) and still facilitate the exchangability of the catheter over the wire. However, the proximal guide wire port in such designs is generally disposed within the body spaces during in-vivo use. This often renders guide wire exchanges through the guide wire lumen quite difficult and often impossible while the distal positioning of such catheters is maintained.

"Fixed-wire" balloon catheters have a steerable guide wire integrated into the balloon catheter assembly. In this way, the balloon catheter and guide wire may be advanced into distal anatomy as a unit. The guide wire may be torqued to cause a rotational response at the tip; although, in fixed wire catheters the guide wire is somewhat restrained in the limits of its movement such that it is not truly independent of the catheter. For example, the guide wire in a fixed wire balloon catheter usually may not be advanced or retracted axially and has a limit in the number of rotating turns that can be imparted to the wire relative to the catheter.

A single lumen may be provided in fixed wire balloon catheters, serving the function both as a balloon inflation lumen and a guide wire lumen. This provides a more modest profile when compared with multilumen catheter designs. In order to effectuate balloon inflation in a fixed wire balloon design having only a single lumen, the distal end of the balloon is sealed onto the wire. This may be accomplished either by affixing the balloon to the wire or by limiting the clearance between the wire and the balloon.

More recent balloon catheter designs are generally referred to as "single-lumen" catheters. Such single lumen catheters may include a guide wire that is independent of the catheter. The single lumen of "single lumen" catheters facilitates balloon inflation and at the same time is co-axial with the guide wire, as is generally the case in many fixed wire balloon catheter designs. However, this embodiment of the "single lumen" balloon catheter often has a valve mechanism provided on the catheter (or on the wire) such that a fluid seal may be selectively achieved between the wire and the catheter. Thus, the wire is slidable within the lumen and may be advanced and torqued relatively independently of the catheter in order to select and track to remote sites. Yet, the lumen may be tightly sealed onto the wire via the valve mechanism provided for balloon inflation when desired.

One example of a single lumen balloon catheter having a valve situated on the guide wire for effecting a seal at the balloon catheter tip is found in U.S. Pat. No. 5,304,198 to Samson, et al. Samson discloses a single-lumen balloon catheter having a valve seat on the distal end of the catheter, distal of the balloon, which may be operated by a control wire having a valve plug disposed on the wire. The valve seat may be engaged by the valve plug from either direction, depending on the installation of the control wire. Pushing or pulling on the wire, depending on the initial orientation of the wire relative to the valve seat, will seat the valve plug in the valve seat and allow the introduction of fluid through the catheter lumen to inflate the balloon.

Other examples of balloon catheters that generally have one lumen that is coaxially disposed about the guide wire and is also used for balloon inflation are disclosed in the following references: U.S. Pat. No. 5,171,221 to Samson;

U.S. Pat. No. 4,606,347 to Fogarty, et al.; U.S. Pat. No. 5,085,636 to Burns; U.S. Pat. No. 4,813,934 to Engelson, et al.; and U.S. Pat. No. 5,437,632 to Engelson, et al.

Delivery Catheter Overview

Although balloon catheters may facilitate medical treatment by providing a fluid expandable balloon on a distal portion thereof, delivery catheters facilitate medical treatment by providing a conduit with one or more distal ports for remote delivery of diagnostic or therapeutic agents. Such agents may be fluids, such as drugs or radiopaque dyes, or devices, such as wires or vaso-occlusive coils.

Delivery catheters are often delivered to remote in-vivo locations in a manner similar to that used for over-the-wire balloon catheters. A steerable guide wire is extended to a point at or near the desired treatment site. Delivery catheters are usually provided with a lumen that allows the delivery catheter to co-axially track over the wire to the desired site.

For "end hole" delivery catheters, agents such as fluids may be delivered out a distal end port provided. Fluid agents may be so delivered either through the co-axial space between the catheter and the wire or through the open lumen with the wire removed.

One example of a delivery catheter having an end hole port for fluid delivery is disclosed in U.S. Pat. No. 4,739,768 to Engelson. Engelson discloses a catheter which can be guided over a guide wire along a tortuous path of at least about 5 cm through vessels of less than about 3 mm lumen inner diameter. Engelson further discloses delivery of fluid materials through a lumen provided after the guide wire is withdrawn. The fluid materials may include radio-opaque agents, vaso-occlusive agents, such as a suspension of collagen fibers, which can be used to produce small-artery vaso-occlusion, and pharmacological agents.

Alternatively or in addition to end holes for such fluid or device delivery, "side hole" delivery catheters may have one or more ports near to and proximal of the catheter distal end. These ports may be in fluid communication either with a single lumen or with more than one lumen. These multiple distal ports are often in a desired spatial arrangement, such as at a predetermined spaced interval longitudinally along the catheter axis, in a spiral arrangement, etc.

Balloon/Delivery Catheter Overview

Some medical conditions may require both a balloon catheter and a fluid delivery catheter to facilitate treatment. For instance, a patient may need a balloon inflation for performing angioplasty to re-open blocked vessels. Simultaneous or serial delivery of drugs such as thrombolytic agents, or of radiopaque dye for visualization, may be desirable at the angioplasty site. Or, a patient treatment may require fluid communication through a distal catheter port, which port may be desirably isolated from certain flow dynamics, such as from branching vessels other than a targetted vessel. This may be desirable for instance for isolated drug delivery out the port and only into a targetted side branch vessel, or for radiopaque dye delivery into that side branch.

In part to provide solutions to these needs, catheters have been disclosed having a fluid delivery port adjacent the balloon such that the balloon may be inflated against a vessel wall to isolate the delivery site from hemodynamics opposite the balloon from the port. Such a port may be located distally of the balloon. Such isolation may be accompolished in a guide wire lumen in the general over-the-wire balloon catheter designs. Additionally, balloon catheters have been disclosed having lumens ending in side ports disposed proximally of the balloon catheter. Balloon catheters of the types just described may be generally referred to as "balloon/delivery" catheters, although particular references may use different descriptors.

One example of a dilation-drug delivery catheter is disclosed in U.S. Pat. No. 5,415,636 to Forman. Forman describes a dilation-drug delivery catheter having a dilation portion for dilating a stenosis and a drug delivery portion for delivering antithrombolytic, antiproliferative, or any other type of medication to the dilation site. The drug delivery portion of the catheter is located within the dilation portion, which can be retracted to reveal the drug delivery portion distal thereto after dilation. occlusion balloons described in the reference are preferably provided on the drug delivery portion to isolate the dilation site during drug delivery. A dilatation lumen, a drug delivery lumen, a guide wire lumen, and an inflation lumen in an inner catheter shaft are provided in the catheter described.

Another example of a balloon catheter having a proximal port connected to a lumen is disclosed in U.S. Pat. No. 5,413,581 to Goy. Goy discloses a balloon dilatation catheter having a first lumen extending along the entire length of a shaft, which lumen is connected to a pump and, at the distal end of the catheter, to the inside of the balloon. Through this lumen there also passes a support wire connected firmly to the catheter at the catheter's distal end. The shaft has an additional lumen which opens outwards of the catheter via an opening behind the proximal end of the balloon. Goy discloses that a controllable guide wire can be introduced into this additional lumen via an attachment piece, and that a measuring apparatus or an apparatus for introducing a contrast medium or drug can as well be connected to this additional lumen.

Another dilatation balloon catheter having an infusion lumen is found in U.S. Pat. No. 5,368,567 to Lee. Lee discloses a dilatation catheter having two or more associated fluid carrying tubes, the operative or distal end of one of which supplies fluid to inflate an expansible balloon and the operable or distal end of the other of which supplies an injectable dye or contrast enhancing fluid adjacent the proximal end of the balloon. The catheter embodiments disclosed by Lee also include a guide wire lumen separate from the balloon inflation lumen. The proximal end of the short guide wire lumen preferably begins adjacent the distal opening of a hollow tube lumen for injecting contrast medium proximal of the balloon. The distal end of the short guide wire lumen terminates distally of the sealed balloon.

U.S. Pat. No. 4,983,166 to Yamawaki discloses a balloon catheter having a balloon and a main passage ending in an opening behind the balloon. The reference discloses that, with the balloon inflated, drugs may be delivered through the opening and into other branches than that in which the balloon catheter tip is placed. Yamawaki discloses use of a circulatory curved tip end portion of the balloon catheter for inserting the catheter from a thicker artery into a thinner artery diverging from the thicker artery at an acute angle. The reference further discloses that a guidewire may be placed in the drug delivery passageway and out the opening behind the balloon, but does not otherwise disclose a guidewire lumen for tracking of the catheter over a guidewire to a remote in-vivo location.

None of these references disclose a balloon/delivery catheter having a single lumen for both balloon inflation and guide wire tracking, and having a second lumen for delivery of therapeutic or diagnostic agents to and out a delivery port proximal to the balloon.

Vaso-Occlusion Agents & Delivery Techniques

One example of a medical treatment that has, for certain applications, been facilitated by delivery of therapeutic treatments through balloon/delivery catheters is artificial vaso-occlusion.

Artificial vaso-occlusion or embolization is a medical treatment that often involves locally delivering an agent to a desired site. The agent therein causes a physiological occlusive response to flow or otherwise blocks or fills a body space. Different sites in the body where vaso-occlusion treatments have been used include aneurysms, blood vessels, and arterio-venous malformations.

Accurate placement during the delivery of vaso-occlusive agents is critical, since inaccurate placement of the occlusive device may undesirably occlude regions were continued flow must or should be maintained. Appropriate placement is especially important where an agent is relatively fluid and may migrate from the desired site if exposed to physiological flow. It is at least in part for this reason that it is often desirable to isolate target delivery sites from flow dynamics of adjacent vasculature when delivering vaso-occlusive agents.

Examples of various chemicals that have been used for in-vivo artificial vaso-occlusion include ethanol, estrogen, polyvinyl acetate ("PVA"), ethylene vinyl alcohol ("EVAL"), cellulose acetate polymer, or combinations thereof. Known delivery techniques for such vaso-occlusive agents include delivery through microcatheter-type delivery catheters, and delivery through balloon/delivery catheters having delivery ports distal to expandable balloons.

One reference to arterial embolization through a balloon catheter with a passage ending in an opening proximal of the balloon is in U.S. Pat. No. 4,983,166 to Yamawaki (introduced above). However, as mentioned above, Yamawaki does not disclose a means for tracking the balloon catheter over a guidewire to a remote site, but instead uses a circulatory curved tip for subselectivity of side branches.

Another example of an embolization treatment via balloon catheter delivery of chemical embolizing agents in the renal arteries is disclosed in "Nonsurgical Treatment of AVM: Development of New Liquid Embolization Method," Takahashi, et al., Suzuki J., ed., Advances in surgery for cerebral stroke, Tokyo, Japan: Springer-Verlag 1988:215–224. Takahashi discloses percutaneous delivery of conjugated estrogen diluted in 25% ethanol and polyvinyl acetate ("PVac"). According to the disclosure, PVac, when diluted in alcohol, becomes gelatinous in one second upon contacting water. Disclosed treatment methods included injections of PVac during proximal occlusion using slow leaking double lumen balloon catheters after 20 minute infusion of alcohol.

Other documents that disclose examples of balloon catheter aided chemical delivery techniques for artificial vaso-occlusion include: "Experimental Investigations Concerning a New Liquid Embolization Method: Combined Administration of Ethanol-estrogen and Polyvinyl Acetate" by Sugawara, et al., Neurol Med Chir (Tokyo) 33,71–76, 1993; "A New Liquid Material for Embolization of Arteriovenous Malformations" by Taki, et al., AJNR 11:163–168, January/February 1990; "Direct thrombosis of aneurysms with cellulose acetate polymer (Part I: Results of thrombosis in experimental aneurysms)" by Mandai, M.D., et al., J Neurosurg 77;497–500, 1992.

None of these references discloses delivery of a vaso-occlusive agent through a lumen proximally of a balloon in a catheter assembly that is trackable to a remote in-vivo site over a guidewire. There is a need for such a balloon/delivery catheter for achieving isolated vaso-occlusive agent delivery in tortuous anatomy where distal migration of the delivered agent is not desired. There is also a need for a balloon/delivery catheter having a single lumen for facilitating balloon inflation and guide wire tracking and having a second lumen ending in a port proximal to the balloon for delivery of diagnostic and therapeutic agents.

SUMMARY OF THE INVENTION

This invention is a medical catheter that comprises a body having on its distal end portion an expandable balloon. An inflation/wire lumen extends between a port on the proximal portion of the catheter and a distal guide wire port located distal to the balloon. The inflation/wire lumen is also fluidly coupled to the balloon. At least one delivery lumen also extends from the proximal end portion of the body and has a delivery port located proximal to the balloon. The delivery port provides for fluid communication between the delivery lumen and external body spaces.

In one embodiment of the invention, a wire with a valve plug is slidably disposed within the inflation/ wire lumen to form an adjustable pressure seal at a valve seat on the distal end of the catheter. This wire allows fluid within the guidewire/inflation lumen to be pressurized by a pressurisable fluid source in order to effectuate balloon inflation.

In another embodiment of the invention, a vaso-occlusive agent delivery assembly is provided having a balloon/delivery catheter with an expandable balloon on a distal end portion fluidly coupled to a proximal pressure source, a guidewire lumen with a guidewire port distal of the balloon, and a delivery lumen with a delivery port proximal of the balloon for delivering a vaso-occlusive agent. The assembly further comprises a pressurizable vaso-occlusive agent source coupled to a proximal port of the delivery lumen such that a vaso-occlusive agent may be delivered through the delivery lumen and out the delivery port proximally of the expanded balloon. In one variation of this embodiment, the balloon/delivery catheter of the vaso-occlusive agent delivery assembly may comprise a single inflation/wire lumen that is both fluidly coupled to the balloon and adapted to co-axially receive a guidewire. In another variation of the embodiment, the assembly includes a guidewire co-axially coupled into the balloon catheter's guidewire lumen.

Also contemplated as a part of the present invention are preferred methods of use of the embodiments described.

DETAILED DESCRIPTION OF THE INVENTION

One embodiment of the invention is a balloon catheter having a first lumen for both balloon inflation and for guide wire tracking, and also having a second lumen ending in a delivery port proximal of the balloon. The delivery port is the site through which therapeutic or diagnostic agents may be delivered. In such a balloon catheter design, the guide wire is desirably slidable within the first lumen while tracking to a selected site, and is further used to effectuate a seal in the first lumen to inflate the balloon with pressurized fluid.

Figure 1A:
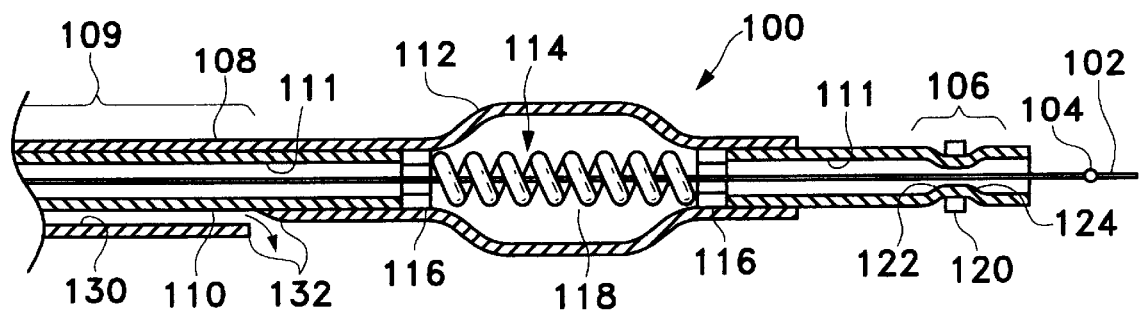
FIG. 1A shows a sectional side-view of a balloon/delivery catheter embodiment of the present invention.
Figure 1B:
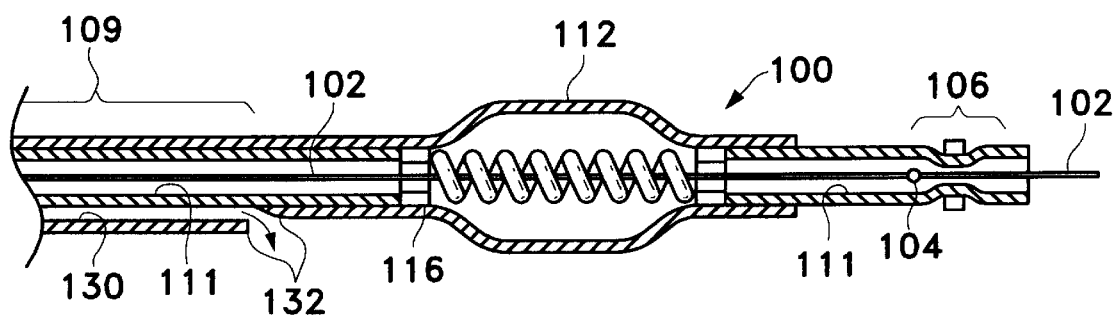
FIG. 1B shows a sectional side-view of the balloon/delivery catheter of FIG. 1A in an alternative configuration.

FIGS. 1A and 1B show the distal portion, generally designated (100), of a catheter assembly made according to one embodiment of the invention. The catheter shown here, in so far as it relates to the "single lumen" configuration for balloon inflation and guide wire tracking, is similar to that disclosed in U.S. Pat. No. 5,304,198. FIG. 1A depicts the distal end of the catheter assembly when the guidewire has been inserted with the valve plug (104) distally of the valve section (106). FIG. 1B shows the same catheter assembly (100) with the guidewire (102) having valve plug (104) positioned proximately of valve section (106).

Referring to FIG. 1A, the catheter body is made up of an outer, thin-wall tubing (108) and an inner tubing (110). The balloon body (112) encompasses the balloon inner member (114), which balloon under member (114) is made up of balloon inner member end sections (116) and a fluid permeable member (118). Distally of balloon (112) is located the valving for the catheter. The valving is a valve section (106) which may be made up of a simple tube having a metal band (120) located so as to form a valve surface (122) proximally of the metal band (120) on the interior of the lumen and a valve surface (124) distally of the band (120). Shown proximally of balloon (112) is delivery lumen (130) which is shown to terminate at its distal end at distal delivery port (132).

The catheter (100) has a body section (109) proximal of the balloon section which desirably is made up of an outer tubing (108) which is strong and flexible and an inner tubing member (110). There are a number of materials which are suitable for the outer tubing, e.g., high density polyethylene (HDPE), low density polyethylene (LDPE), certain highly cross linked silicones, polyesters (including Nylon), polyvinyl chloride, high molecular weight polyurethanes, polyamides, polyimides, or suitable blends or co-polymers thereof. One particularly desirable type of material for the outer tubing is a polyamide block co-polymer such as PEBAX™. Also, a polyimide may be particularly desirable in that it has a substantial axial strength and is therefore quite "pushable" and also maintains the catheter lumen open even under the severest of pressure. The distal portion of this catheter body is preferably of a flexible material, such as flexible derivatives of the materials just described, for instance low density polyethylene.

Although a two layered catheter body (109) is shown, inner tubing member (110) is not a required portion of the inventive device but is desirable. The inner tubing member (110) may be coextruded or otherwise integrated with the outer tubing (108) or may be a discrete member. The inner tubing member (110) may be a lubricious polymer. Suitably lubricious materials include polysulfides and polyfluoroethylenes. Suitable polyfluoroethylenes include polytetrafluoro-ethylene, fluoroethylene copolymers having perfluoroalk-oxy groups, copolymers of tetrafluoroethylene, hexa-fluoropropylene, and copolymers of ethylene and tetrafluoroethylene. Highly desirable are copolymers of tetrafluoroethylene and hexafluoroethylene.

Where catheter body (109) is provided with inner tubing member (110) as a laminate or coextrusion with outer tubing (108), delivery lumen (130) may be formed using methods as may be apparent to one of ordinary skill. However, some preferred alternative methods for forming delivery lumen (130) are herein provided.

One example of forming delivery lumen (130) is by providing a die/mandrel configuration (not shown) to yield delivery lumen (130) between outer tubing (108) and inner tubing member (110). Such a die/mandrel configuration could alternatively yield delivery lumen (130) when there is only one tubing forming the catheter body, as opposed to having outer tubing (108) and inner tubing member (110). Still alternatively, a wire (not shown) may be pulled through an extruder die along with the molten, yet cooling extruded polymer or polymers, such that removal of the wire after extrusion may leave delivery lumen (130). A copper wire is suitable in this method due to the ability to draw down the metal for removal. The wire may also be coated with an oxidated layer or releasing agent which may aid in the removal of the wire from the extrusion.

Also, a method employing heat shrink tubing or other known lamination method may be used to form outer tubing (108) and inner tubing member (110) together as catheter body (109). Similar techniques to those just described may be employed to form delivery lumen (130) in these lamination methods. For example, a copper wire may be threaded between independent tubings (108) and (110) prior to heat shrinking. Outer tubing (108) may then be heat shrunk over inner tubing member (110) and the copper wire. Subsequent withdrawal of the copper wire leaves delivery lumen (130).

Delivery port (132) also may be formed in catheter (100) as may be apparent to one of ordinary skill. One acceptable method is a notching method, which starts with a dual lumen piece of tubing that is cut to a predetermined length. Delivery lumen (130) of the dual lumen piece may be trimmed away from an end portion of the dual lumen piece. In this technique, a razor blade or other cutting means may be fixtured for selective cutting of delivery lumen (130) such that the resulting delivery port (132) has a preferred shape. The resulting tubing has delivery lumen (130) ending in delivery port (132). The untrimmed portion, extending distally beyond delivery port (132) and forming inflation/wire lumen (111), may thereafter be adapted to the components of the catheter distal end portion that are herein described, including balloon (112), as may be apparent to one of ordinary skill.

In addition to the desirable balloon/delivery catheter embodiment shown in FIGS. 1A and 1B, it is further contemplated that a plurality of delivery lumens such as that shown at (130) may be provided. Similarly, delivery port (132) may be only one of a plurality of such ports proximal of the balloon, which ports may be in communication with a common lumen or with a multiplicity of lumens. Such a use of multiple lumens and/or ports in the present invention may be preferred when delivery of an agent proximally of the balloon at more than one discrete site is desired.

Balloon (112) may be made out of a variety of materials. Preferably, balloon (112) is a compliant material such as a silicone or rubber such as latex. Another suitable alternative, however, may be a radiated polyolefin tubing, such as low density polyethylene, high density polyethylene, polypropylene, polybutene, or interpolymers or mixtures of these polymers. Balloon (112) may be formed using conventional methods, preferably using methods and materials to impart "isoaxial" properties to the balloon, such that the length of the formed balloon does not change substantially when pressurized for inflation.

The balloon inner member assembly (114) shown in FIGS. 1A and 1B has two ends (116) and a coil spring (118). The ends allow mounting of the balloon inner member (114) in the sections of the catheter having reasonably constant diameter. The inner diameter may be large enough to pass the valve plug (104) therethrough or may be smaller to allow only the guidewire to pass. The ends have, of course, a lumen allowing a guidewire to pass completely through the ends and through the intermediate coil (118). The ends (116) may be attached to the coil (118) by any suitable means including gluing, shrink wrapping, heat welding, solvent welding, and a host of other ways. The spring (118) involved is one having an inside diameter at least larger than that of the guidewire passing through it. Typically the inside diameter of coil (118) would be 0.020 to 0.035 of an inch. The diameter of coil wire typically would be in the region of 0.003 to 0.005 of an inch. The coil itself (118) may be wound in such a way that there is little space between windings. Ideally, the windings are flush with each other. That is to say the pitch of the coil is equal to the diameter of the wire making up the coil. The coil may be of any suitable material although gold alloys, silver alloys, platinum alloys, and other biocompatible materials having significant springiness are appropriate in this service. Polymeric materials or carbon fiber materials having the appropriate physical characteristics are also quite workable.

As acceptable alternatives to coil (118) for inner member assembly (114), other structures for bridging the proximal and distal balloon regions are contemplated as falling within the scope of the present invention. For example, a braid (not shown) may be substituted for coil (118). An inner tubing coaxial to the coil and having orifices to permit fluid flow into the balloon may also be used (not shown).

The valve portion of the catheter assembly is preferably inserted into the portion of the balloon having relatively constant inner diameter. It is held in place by heat welding or gluing or other suitable process. The valve section (106) with its ring (120) and proximal valve surface (122) and distal valve surface (124) may be made by the following procedure, which is provided as an example. A polymeric tube having an inside diameter larger than the guidewire is stretched over a mandrel such as a suitably sized stainless steel wire. The ends are locked over the mandrel by heating. A temperature of about 600° F. may be appropriate when the chosen polymer is a polyimide. A ring having an appropriate inside diameter is slipped over the tubing. The locked ends of the tubing are cut off to allow the tubing to recover its original dimensions. Polyimide tubing recovers fully by heating it to about 550° F. The ring may be of gold, platinum, platinum-tungsten alloy, stainless steel, or other suitable and, preferably, radioopaque materials. The tubing, upon return to its former diameter, forms distal and proximal surfaces adjacent the ring which serve as valve surfaces for the plug residing on the guidewire. This distal structure substantially eliminates the possibility of "accordioning" when the distal valve surface (124) is used as the valve seat.

FIG. 1B simply shows the insertion of the guidewire (102) from the proximal end of the catheter so to allow the valve plug (104) to seat against the proximal valve surface (122). In this instance the valve is seated by pushing the guidewire (102) distally prior to filling the balloon (112) with a fluid via the catheter lumen.

Wire (112) is preferably a guide wire of a conventional type. However, the present invention contemplates using a wire strictly for purposes of achieving a valve seal for balloon inflation. Where wire (112) is not a conventional guide wire, conventional methods of delivering the balloon device to the desired site may be used.

Figure 2:
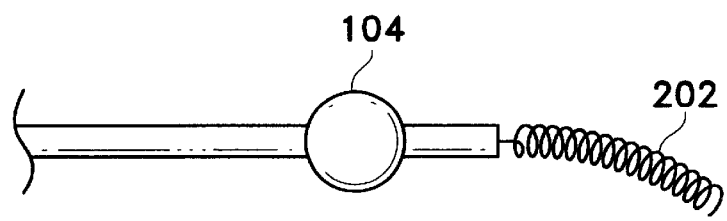
FIG. 2 shows a diagrammatical perspective view of the distal end of a preferred guide wire assembly for use in the balloon/delivery catheter shown in FIGS. 1A and 1B.

The present invention contemplates shapes of valve plug (104) on wire (112) that adequately mesh with the valve surfaces formed in valve section (106). A generally spherical surface is adequate and desirable. Moreover, in addition to the relatively simple guidewires of varying thicknesses as are known in this technology and shown in FIGS. 1A and 1B, the guidewire used in this invention may additionally have a flexible tip (202) as is shown in FIG. 2. These flexible tips are well known, and are generally used with the aid of fluoroscopy to advance the catheter through the vasculature.

Other designs are well known in the art for achieving "single lumen" balloon inflation/guide wire tracking. For example, other balloon catheter designs of the type shown in the following documents may be effectively substituted with preferred embodiments described herein in order to achieve a single lumen for balloon inflation and guide wire coupling in the present invention: U.S. Pat. No. 5,171,221; U.S. Pat. No. 5,304,198; U.S. Pat. No. 5,085,636; U.S. Pat. No. 4,606,347; U.S. Pat. No. 4,813,934; U.S. Pat. No. 5,437,632. The disclosures in each of these documents are herein incorporated into this specification in their entirety by reference.

The catheter assembly of this embodiment may be operated in a similar fashion to other valve balloon catheters. In such operation, distal loading of valve plug (104) relative to valve section (106) may be desirable when high tortuosity in the vascular presents a particular challenge in reaching a desired site. In this configuration, the catheter (with the collapsed balloon) may be moved distally along the guidewire to an intermediate site, and the guidewire may be again introduced farther into the vasculature until a desired site is attained.

Alternatively, proximal loading of valve plug (104) relative to valve section (106) may be more desirable for other circumstances. Additionally, the inventive catheter may be used in conjunction with other types of guidewires of compatible size in inflation/wire lumen (111) in order to gain access to the vascular anatomy. In such combinations, however, the conventional guidewire must be replaced in lumen (111) with the guide wire of the present invention having valve plug (104) to create a pressure seal for balloon inflation.

In general use, the guidewire may be advanced into the vasculature to a desired site, and the catheter body is tracked over the guidewire. The location of the guidewire and the balloon within the vessel may be determined by conventional radiology techniques. Once the balloon is at the desired site within the vessel, the catheter lumen is flushed by injecting fluid through the catheter lumen. The valve plug (104) is seated against the distal valve surface (124) or the proximal valve surface (122), depending upon the end from which the guidewire was introduced, by axially manipulating the guidewire to thereby block the distal opening of the catheter tube. The balloon is then inflated by injecting fluid through the catheter lumen. If desired, controlled distal leakage of the fluid from the catheter tip may be achieved by a slight adjustment in the tightness of the seating between valve plug (104) and the respective valve seating areas. The balloon may be deflated by withdrawing fluid from the catheter lumen.

Some clinical situations require that site-specific drugs, such as urokinase for clot dissolution, or contrast materials for fluoroscopic imaging be delivered through the catheter before or after a balloon inflation is performed. Using the inventive catheter embodiment of FIG. 1A and FIG. 1B, such fluids may be delivered either through lumen (111)

distally of the balloon, or through lumen (130) and out delivery port (132) proximally of the balloon.

Using the inventive balloon/delivery catheter as an "end-hole" infusion catheter, agents may be delivered through lumen (111) and out the catheter's distal end, if so desired. In most such "end-hole" infusion applications, the guide wire must be removed from the lumen or at least advanced distally so the valve plug, if there is one provided on the wire, is not a hindrance to flow.

The present invention also allows for novel "side-hole" delivery mechanisms of drugs, contrast, occlusive agents, or other treatment modalities. Where flow of the agent is desirably to be isolated from distal flow, the agent may be delivered proximally of the inflated balloon through lumen (130) and out delivery port (132). This is because the balloon may be inflated to isolate the distal body space (such as lumenal space) from the proximal space surrounding the catheter relative to the balloon. Subsequent flow thorugh lumen (130) is thereby isolated from regions distal to the balloon. This may be particularly desirable when side branches are targetted and a typical delivery catheter can not be seated there and/or distal flow through the native trunk vessel would render local delivery in such sites difficult.

To summarize the beneficial features of the novel catheter design shown in FIGS. 1A and 1B, delivery lumen (130) is provided specifically for the delivery of a drug or other fluid or agent, proximally of the inflated balloon, simultaneously or in series with balloon dilatation or other therapeutic or diagnostic inflation. Because the embodiment shown in FIG. 1A and FIG. 1B incorporates a single lumen for guide wire tracking and balloon inflation, the resulting catheter may comprise only two lumens that functionally provide for four catheter needs. First, a lumen of the catheter can be slideably coupled with a guide wire for distal tracking. Second, a pressure seal may be achieved in a lumen for balloon inflation. Third, agents such as fluids may be delivered through a lumen separate from the guide wire or inflation lumens and locally isolated proximal to the balloon. Fourth, such agents may also be delivered distally of the balloon through the guidewire lumen when the balloon is not being inflated.

This novel catheter design of FIGS. 1A and 1B may allow for a significant reduction of profile of the catheter shaft when compared to other designs that would have more lumens serving the listed functions. Alternatively, the design may allow for a larger lumenal inner diameter for increased delivery rate in a catheter of a given french size.

Figure 3:
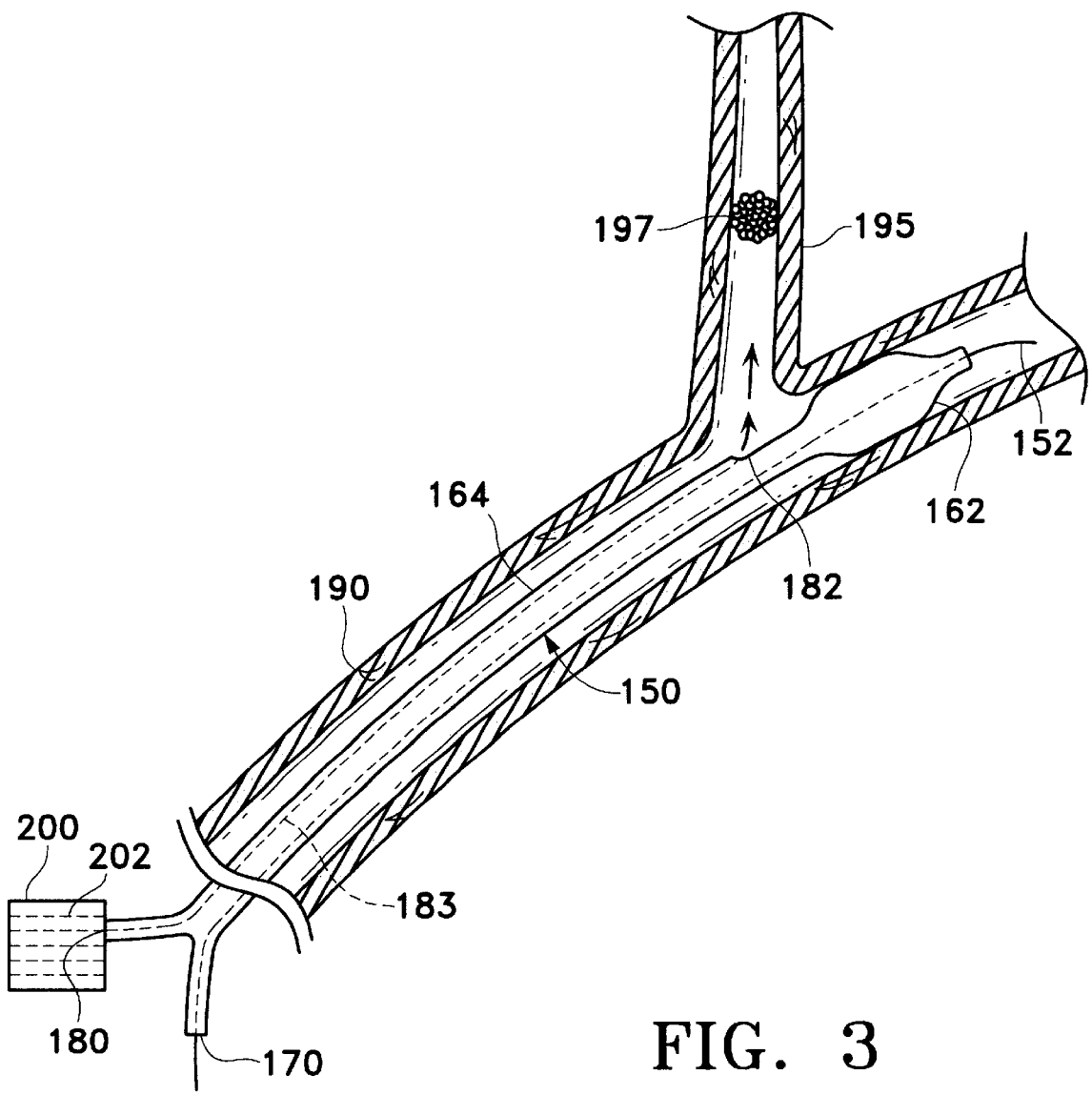
FIG. 3 shows a perspective view of a vaso-occlusive agent delivery assembly embodiment of the present invention, wherein a vaso-occlusive agent is shown during delivery through a lumen of a balloon/delivery catheter, out a port of the lumen disposed proximally of an expanded balloon, and into a sidebranch vessel.

FIG. 3 shows a further embodiment of the present invention wherein a balloon/delivery catheter is a part of a novel vaso-occlusive agent delivery assembly. This embodiment contemplates passing a vaso-occlusive agent through a port of a catheter lumen located proximal of an expandable balloon in a catheter that is trackable over a guidewire or has a guidewire incorporated therewith in a "fixed-wire" design.

The vaso-occlusion agent delivery assembly of the embodiment shown in FIG. 3 may be desirable for many purposes. Preferably, the novel apparatus is designed for use in delivering vaso-occlusive agents into target vessels or aneurysms that branch laterally off of the native trunk vessel and proximal to an expandable balloon of the catheter.

For example, such a delivery mechanism may be desirable where it is critical to ensure that there is no physiological response to the treatment in areas downstream of the treatment site. Also, this novel apparatus and allows for a balloon inflation to fix the catheter positioning relatively firmly during delivery of the agent. This may be particularly a desirable feature where the force required to deliver the agent (such as from pressure in the case of fluid delivery) is of such a magnitude as to deflect an otherwise not anchored delivery catheter. Such a force on the catheter and subsequent movement of its positioning is generally referred to as "recoil," and may result in undesirably inaccurate placement of the vaso-occlusive agent.

The expandable balloon of the balloon/delivery catheter is preferably placed distal to the desired branch or aneurysm and is there expanded, at least to partially radially engage the vessel wall. Preferably the balloon forms a circumferential seal to flow through the vessel at the inflation site. A vaso-occlusive agent is delivered through a lumen ending in a delivery port proximal of the inflated balloon, such that flow of the agent is primarily into side branches proximal of the vessel-occluding balloon. "Single-lumen" designs, such as that previously described above and shown in FIG. 1A and FIG. 1B, represent one preferred mode of this embodiment shown in FIG. 3. However, along with having at least one delivery lumen with at least one port disposed proximally of a balloon, the rest of the balloon catheter design may be a "single lumen" design, an "over-the-wire" design, or a "fixed wire" design as regards the guidewire and balloon inflation lumen or lumens. Regardless, it is crucial that the structure accomadate a steerable guidewire, either slideably in a lumen for co-axial tracking or in a more integrated or fixed manner. Such steerable guidewire coupling is required in order to aid in the proper placement of the balloon in vaso-occlusion procedures requiring high accuracy in placement.

Referring to the details of FIG. 3, catheter (150) is shown to comprise a balloon (162) at a distal end of a catheter body (164). The body (164) has a delivery lumen, the central axis of which is shown in phantom at (183). The delivery lumen has a distal delivery port (182) disposed proximally of the balloon (162) and has a proximal delivery port (180) located on the proximal catheter end and is operational outside of the body.

A guide wire (152) is shown in phantom extending through a wire lumen (not shown) of the catheter, and is shown in perspective view distal to the catheter. If the wire lumen is an inflation/wire lumen of a single-lumen catheter design type, the guide wire preferably comprises a valve plug for sealing the catheter during balloon inflation, as has been previously discussed. The catheter/wire configuration shown in either FIG. 1A or 1B, and the wire shown in FIG. 2 are highly desirable designs for use in this embodiment. However, as mentioned above, other guidewire/inflation lumen configurations are contemplated as within the scope of the current invention, so long as the catheter is trackable over or integrated with a guidewire.

As is shown in FIG. 3, in a preferred mode of operation, the balloon resides co-axially within a native vessel (190) which has a first sidebranch (195) extending laterally from the sidewall of the vessel. The balloon is inflated to engage the vessel wall distally of the sidebranch (195) such that distal delivery port (182) is positioned functionally adjacent sidebranch (195).

In positioning the balloon at a desired location distally of the target site, a radiopaque marker such as a gold marker may be provided, perhaps central or proximal to the balloon's length, and may be used for flouroscopic visualization. Radiopaque dye may be delivered to visualize the target vessel's position relative to the balloon, such as by delivering such dye through the delivery lumen of the catheter and out distal delivery port (182). Alternatively, another delivery mechanism for the dye may be employed, such as through a proximally positioned guiding catheter. Additionally, a radiopaque marker may be provided at or closely adjacent to the distal delivery port (182) in order to percutaneously position that portion of the catheter at a desired location, such as adjacent the target vessel, for example sidebranch (195).

In preferred use, the balloon is inflated prior to delivering a vaso-occlusive agent out of distal delivery port (182). Preferably, the expanded balloon engages the vessel wall at an adequate size, shape, and pressure to ideally achieve all of the following: (1) seal the vessel lumen from fluid flow distally of the balloon, (2) hold the balloon in place during vaso-occlusive agent delivery, and (3) not damage the vessel wall where the balloon is inflated, such as by overstretching the wall. Once the balloon is inflated, a pressurizable fluid source (200) containing a vaso-occlusive agent (202) is coupled to proximal delivery port (180) of the catheter. Upon pressurizing the pressurizable fluid source (200), the vaso-occlusive agent (202) flows from the source, distally through the delivery lumen, toward and through distal delivery port (182), and into the vascular space surrounding body (164).

The present invention contemplates use of any specific type of vaso-occlusive agent that would be conducive to remote in-vivo delivery via the assembly herein described related to FIG. 3. For example, certain vaso-occlusive agents that may be particularly useful when delivered via the assembly of this embodiment include ethanol, estrogen, polyvinyl acetate, ethylene vinyl alcohol, cellulose acetate polymer, collagen, or derivatives or combinations thereof.

Further descriptions of particular vaso-occlusive agents are provided in the following references: "Nonsurgical Treatment of AVM: Development of New Liquid Embolization Method," [conjugated estrogen diluted in 25% ethanol and polyvinyl acetate ("PVac")] Takahashi, et al., Suzuki J., ed., Advances in surgery for cerebral stroke, Tokyo, Japan: Springer-Verlag 1988:215–224; "Experimental Investigations Concerning a New Liquid Embolization Method: Combined Administration of Ethanol-estrogen and Polyvinyl Acetate" by Sugawara, et al., Neurol Med Chir (Tokyo) 33,71–76, 1993; "A New Liquid Material for Embolization of Arteriovenous Malformations" by Taki, et al., AJNR 11:163–168, January/February 1990; and "Direct thrombosis of aneurysms with cellulose acetate polymer (Part I: Results of thrombosis in experimental aneurysms)" by Mandai, M.D., et al., J Neurosurg 77;497–500, 1992. The disclosures of these references are herein incorporated by their entirety by reference.

During delivery of the vaso-occlusive agent, the inflated balloon (162) seals the vessel (190) against flow distally of the delivery site. The tendency for the vaso-occlusive agent (202) to migrate distal to the target site is therefore eliminated or significantly reduced. Rather, the vaso-occlusive agent (202) has an increased propensity to enter the target vessel proximally of the balloon, shown here at sidebranch (195), and forms the desired artificial vaso-occlusion shown at (197).

This novel vaso-occlusion technique may be particularly effective when the trunk vessel is relatively large and has relatively high flow when unoccluded, and also when the native flow in the trunk lumen is in the direction distal of the balloon. Also, although FIG. 3 shown s a vaso-occlusive agent (202) being delivered into a vessel sidebranch (195), delivery of vaso-occlusive agents into other target delivery sites in the body are also contemplated.

Many alterations and modifications may be made by those of ordinary skill in the art without departing from the spirit and scope of this invention. The illustrated embodiments have been shown only for purposes of clarity. The examples should not be taken as limiting the invention as defined by the following claims, which claims include all equivalents, whether those equivalents are now or later devised.

I claim as my invention:

1. A medical device, comprising:
   an inner tubular member having a proximal end, a proximal opening, a distal end, a distal opening, and an inner lumen extending at least partially therethrough;
   an outer tubular member disposed adjacent the inner tubular member, the outer tubular member having a proximal end, a proximal opening, a distal end, a distal opening, and an outer lumen extending at least partially therethrough; and
   a balloon coupled to the outer tubular member adjacent the distal end thereof;
   wherein the inner lumen is in fluid communication with the balloon;
   wherein the distal opening of the inner tubular member is located at a position that is distal of the balloon;
   wherein the distal opening of the outer tubular member is located at a position that is proximal of the balloon.

2. The medical device of claim 1, wherein the inner lumen is in fluid communication with the balloon through a fluid permeable member.

3. The medical device of claim 1, wherein the inner tubular member includes a distal valve section disposed adjacent the distal opening of the inner tubular member.

4. The medical device of claim 3, further comprising a guidewire disposed within the inner tubular member, the guidewire including a valve plug configured to substantially occlude the inner lumen when positioned adjacent the valve section.

5. The medical device of claim 1, wherein at least a portion of the outer tubular member is disposed over the inner tubular member and defines an annular space between the outer tubular member and the inner tubular member.

6. The medical device of claim 5, wherein at least a portion of the outer lumen is defined by the annular space.

7. A medical device, comprising:
   an inner tubular member having a proximal opening, a distal opening, and an inner lumen extending therethrough;
   a sheath disposed over the inner tubular member;
   wherein an annular lumen is defined between the sheath and the inner tubular member;
   wherein the sheath includes a delivery port in fluid communication with the annular lumen; and
   a balloon coupled to the sheath at a position that is distal of the delivery port;
   wherein the inner lumen is in fluid communication with the balloon;
   wherein the distal opening of the inner tubular member is located at a position that is distal of the balloon.

8. The medical device of claim 7, wherein the inner lumen is in fluid communication with the balloon through a fluid permeable member.

9. The medical device of claim 7, wherein the inner tubular member includes a distal valve section disposed adjacent the distal opening of the inner tubular member.

10. The medical device of claim 7, further comprising a guidewire disposed within the inner tubular member, the guidewire including a valve plug configured to substantially occlude the inner lumen when positioned adjacent the valve section.

11. A balloon catheter, comprising:
a first independent tube having a proximal end and a distal end;
a second independent tube disposed within the first independent tube, the second independent tube including an inner lumen extending therethrough, proximal portion, a distal portion, and an inflation portion extending between the proximal and distal portions; and
a balloon coupled to the first independent tube adjacent the distal end of the first independent tube and over the inflation portion of the second independent tube;
wherein an annular lumen is defined between the first independent tube and the proximal portion of the second independent tube;
wherein the first independent tube includes a distal opening located at a position that is adjacent the proximal portion of the second independent tube, the opening being in fluid communication with the annular lumen.

12. The balloon catheter of claim 11, wherein the distal portion of the second independent tube includes a distal valve section.

13. The balloon catheter of claim 12, further comprising a guidewire disposed within the second independent tube, the guidewire including a valve plug configured to substantially occlude the inner lumen when positioned adjacent the valve section.

14. The balloon catheter of claim 11, wherein the inflation portion is fluid permeable.

15. The balloon catheter of claim 11, wherein the proximal portion of the second independent tube includes a distal end and the distal portion of the second independent tube includes a proximal end, and wherein the inner lumen extends through the proximal portion, out of the distal end thereof into the inflation portion, into the proximal end of the distal portion, and through the distal portion.

16. The balloon catheter of claim 15, wherein the inflation portion comprises a coil having an interior region.

17. The balloon catheter of claim 16, further comprising a guidewire extending through the proximal portion, the interior region of the coil, and the distal portion.

18. A balloon catheter, comprising:
an inner tubular member having a longitudinal axis, a proximal portion, a distal portion, a fluid permeable coil extending between the proximal and distal portions;
wherein the coil includes an interior region oriented along the longitudinal axis of the inner tubular member and a lumen;
wherein the inner tubular member defines an inflation lumen extending from the proximal portion, through the lumen of the coil, and out of the distal portion;
a guidewire extending through the proximal portion, the interior region of the coil, and the distal portion;
an outer tubular member disposed over the proximal portion and the coil, and at least partially over the distal portion of inner tubular member;
a balloon coupled to the outer tubular member adjacent the coil;
wherein an annular lumen is defined between the outer tubular member and the proximal portion of the inner tubular member; and
an outlet port formed in the outer tubular member adjacent the proximal portion, the port being in fluid communication with the annular lumen.

19. The balloon catheter of claim 18, wherein the distal portion of the inner tubular member includes a distal valve section.

20. The balloon catheter of claim 19, wherein the guidewire includes a valve plug configured to substantially occlude the inflation lumen when positioned adjacent the valve section.

21. A medical device, comprising:
an inner tubular member including an inner lumen extending therethrough, a proximal portion, an inflation portion, and a proximal portion;
wherein the inner tubular member includes means for slidably receiving a guidewire;
an outer tubular member disposed over at least a portion of the inner tubular member;
a balloon coupled to the outer tubular member;
wherein the inner lumen is in fluid communication with the balloon through the inflation portion;
an annular lumen defined between the outer tubular member and the proximal portion of the inner tubular member; and
a delivery port formed within the outer tubular member at position that is proximal of the balloon, the delivery port being in fluid communication with the annular lumen.

22. A medical device, comprising:
a first independent tube including an inner lumen extending therethrough, a proximal portion, an inflation portion, and a proximal portion;
wherein the first independent tube includes means for slidably receiving a guidewire;
a second independent tube disposed over at least a portion of the first independent tube;
a balloon coupled to the second independent tube;
wherein the inner lumen is in fluid communication with the balloon through the inflation portion;
an annular lumen defined between the proximal portion of the first independent tube and the second independent tube; and
a delivery port formed within the second independent tube at position that is proximal of the balloon, the delivery port being in fluid communication with the annular lumen.

* * * * *